United States Patent
Lange

(10) Patent No.: US 6,379,624 B1
(45) Date of Patent: Apr. 30, 2002

(54) DEVICE FOR THE CONTAMINATION-FREE DELIVERY AND DISCHARGE OF LIQUID

(75) Inventor: Hans Lange, Lambertheim (DE)

(73) Assignee: November Aktiengesellschaft Gesellschaft fur Molekulare Medizin, Erlangen (DE)

( * ) Notice: Subject to any disclaimer, the term of this patent is extended or adjusted under 35 U.S.C. 154(b) by 0 days.

(21) Appl. No.: 09/202,659

(22) PCT Filed: Jun. 26, 1997

(86) PCT No.: PCT/DE97/01331
§ 371 Date: May 10, 1999
§ 102(e) Date: May 10, 1999

(87) PCT Pub. No.: WO98/00718
PCT Pub. Date: Jan. 8, 1998

(30) Foreign Application Priority Data

Jun. 29, 1996 (DE) .......................................... 196 26 234

(51) Int. Cl.[7] .................................................. B01L 3/00
(52) U.S. Cl. ........................ 422/100; 422/99; 422/101; 73/863; 73/864
(58) Field of Search ....................... 422/100; 73/863.25, 73/864.01, 864.02, 864.03, 864.11, 863.23, 863.24

(56) References Cited

U.S. PATENT DOCUMENTS

| | | | |
|---|---|---|---|
| 4,341,568 A | | 7/1982 | Christensen |
| 4,909,992 A | * | 3/1990 | Bjorkman |
| 4,999,164 A | * | 3/1991 | Puchinger et al. |
| 5,092,184 A | * | 3/1992 | Goodell et al. |
| 5,158,101 A | | 10/1992 | Sakka |
| 5,260,030 A | * | 11/1993 | DeVaughn .................. 422/100 |
| 5,496,523 A | * | 3/1996 | Gazit et al. |
| 5,580,529 A | * | 12/1996 | DeVaughn et al. |
| 5,620,660 A | * | 4/1997 | Belgardt et al. |
| 5,620,661 A | * | 4/1997 | Schurbrock |

FOREIGN PATENT DOCUMENTS

| | | |
|---|---|---|
| EP | 0 213 618 | 3/1987 |
| EP | 0 328 859 | 8/1989 |

* cited by examiner

*Primary Examiner*—Jill Warden
*Assistant Examiner*—Brian Sines
(74) *Attorney, Agent, or Firm*—Pearne & Gordon LLP

(57) ABSTRACT

The invention relates to a device for the contamination-free delivery and discharge of liquid into and from a reaction vessel 15, having a tube 1, one end of which [lacuna] designed as a first connection fitting 2 for connection to a pipette or the like and the other end of which has a first opening 3. In order to avoid contamination when the reaction vessel is filled with and drained of liquids, it is proposed that a second connection fitting 4, which is in communication with at least a second opening 8, is provided in the vicinity of the first end.

30 Claims, 6 Drawing Sheets

DEVICE FOR THE CONTAMINATION-FREE DELIVERY AND DISCHARGE OF LIQUID

The invention relates to a device according to the preamble of patent claim 1.

Such a device is known from U.S. Pat. No. 4,341,568.

Moreover, disposable pipette tips are known from the prior art. Such disposable pipette tips are marketed, for example, by the Eppendorf company.

They are used in many analysis processes for separating bonded and solid phases in a reaction vessel with a subsequent washing process for the solid phase. One example is the immunoassay, in which the solid phase may be present in the form of magnetic particles or in the form of so-called "coated tubes". In the case of "coated tubes", the solid phase is at the same time the wall of the reaction vessel. The washing process in each case comprises three steps:

a) sucking out the reaction solution which is to be discarded, the solid phase being retained,
b) adding washing solution,
c) sucking out the washing solution, and, if appropriate,
d) repeating the steps described under letter b and letter c.

Particularly when isolating and purifying nucleic acids with a subsequent amplification reaction, it is necessary for there to be no contamination to the analysis sample during the washing step. The polymerase chain reaction is particularly sensitive to contamination. Such contamination may be caused by aerosols formed when washing solution is being introduced and sucked out and which propagate through the air, resulting in carry-overs from one reaction vessel to the next.

The object of the invention is to eliminate the drawbacks of the prior art. The intention in particular is to provide a device which can be used to carry out contamination-free delivery and discharge of liquids into and from a reaction vessel and with which it is possible to suck out in a controlled manner a liquid supernatant which lies above solid particles which have been deposited at the bottom of the reaction vessel.

This object is achieved by means of the features of patent claim 1. Expedient configurations of the invention result from the features of claims 2 to 16.

According to the invention, the tube is designed so as to taper conically toward the first opening. As a result, it is possible to suck out a liquid supernatant in a controlled manner. When washing solution is being sucked out through the tube, there is no possibility of, for example, nucleic acids which are bonded to magnetic particles being sucked in.

Advantageously, the first connection fitting is situated inside the second connection fitting. This allows a particularly space-saving design of the device.

According to a further feature, the second connection fitting may have a flange. This is used to limit the insertion depth when the device is inserted into a reaction vessel.

Expediently, the second connection fitting is in communication with an annular passage which surrounds the tube, the annular passage parallel to the inner wall of the reactive vessel, thus effecting a seal. A conical section, which is connected to the outer wall of the tube, may adjoin the cylindrical section. In this case, the second opening is advantageously situated in the conical section. The cylindrical section is advantageously designed in such a way that it can be inserted into the reaction vessel.

According to a further feature, the device may be made from conductive plastic. As a result, it is possible to derive a signal which represents the filling level in the reaction vessel and as a result to control the filling level automatically.

According to a particularly advantageous feature, 96 reaction vessels are combined together as a "96-well titration plate". As a result, it is possible to wash 96 different samples at the same time.

Exemplary embodiments of the invention are explained in more detail below with reference to the drawing, in which.

Figure 1:
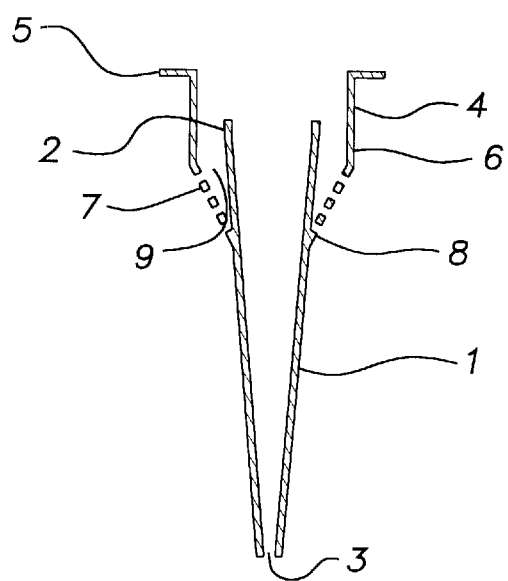
FIG. 1 shows a diagrammatic cross section through a device.
Figure 2:
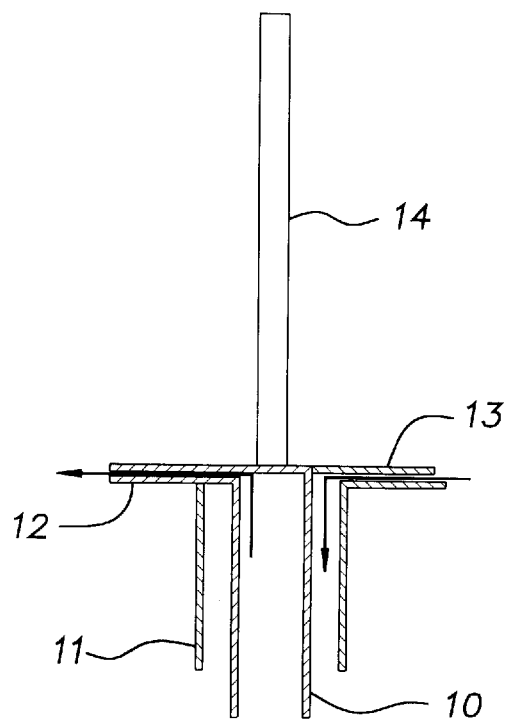
FIG. 2 shows a diagrammatic cross section through a connection piece.
Figure 3:
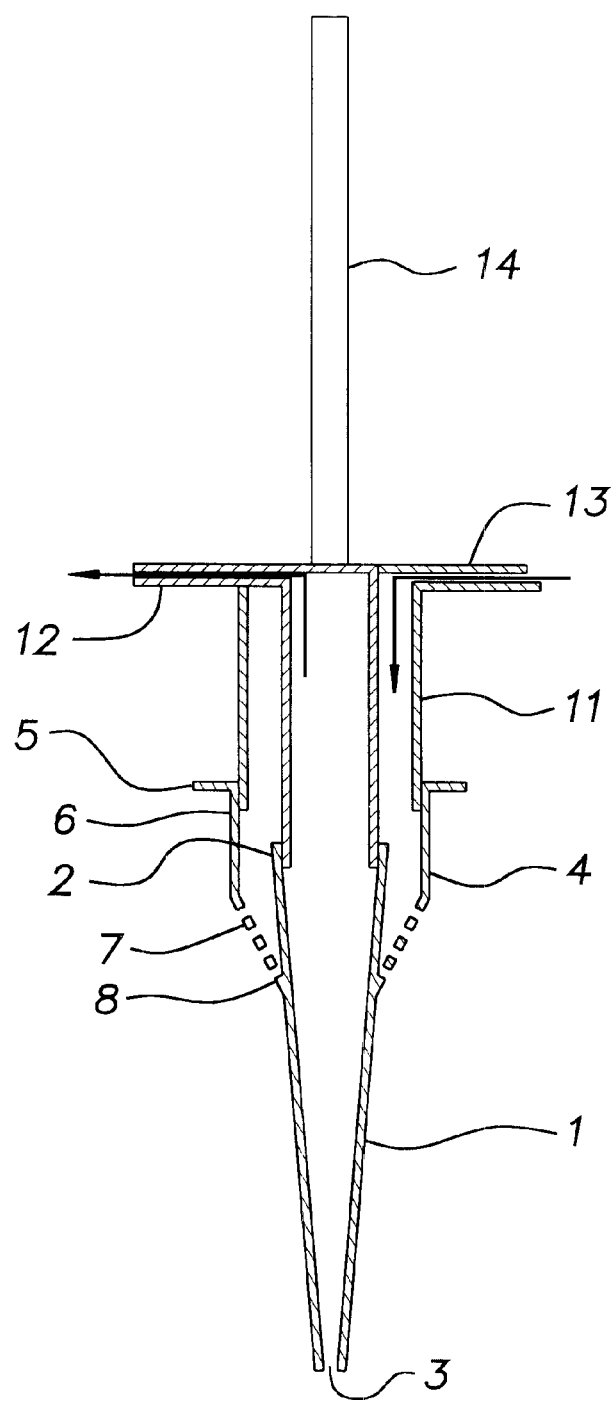
Figure 4:
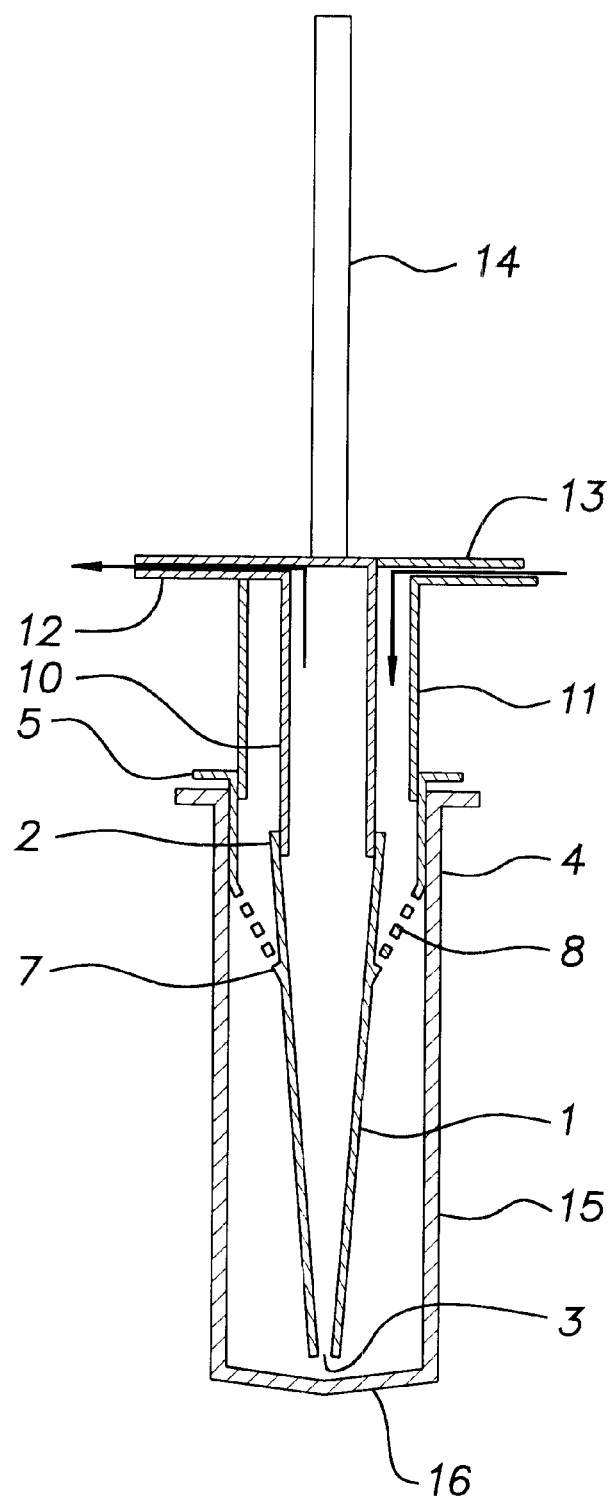
Figure 5:
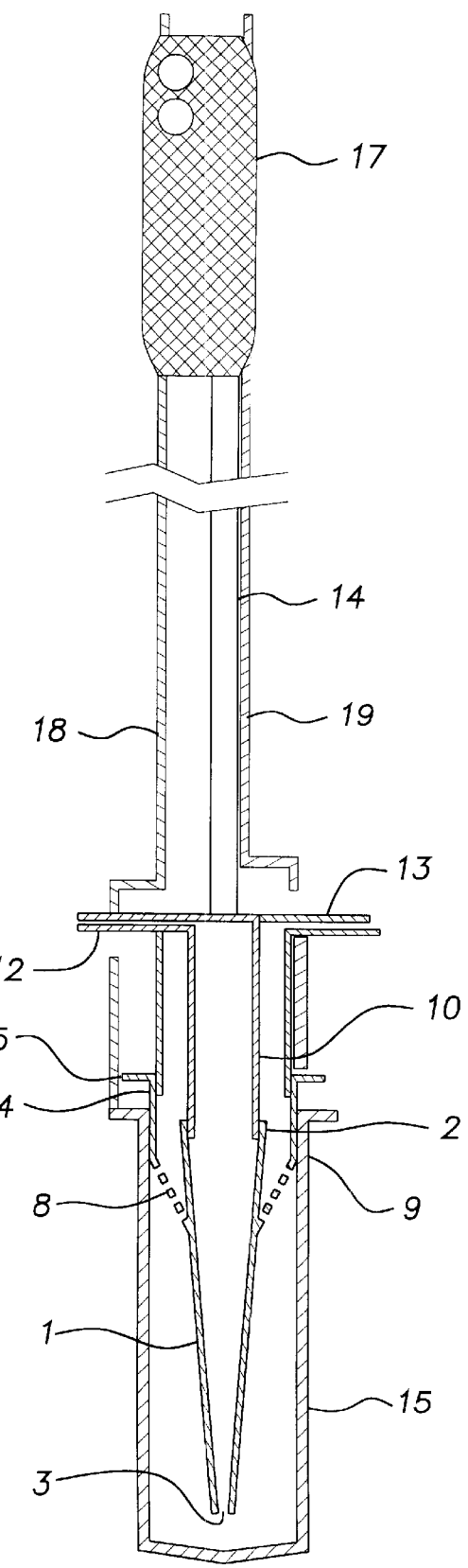
Figure 6:
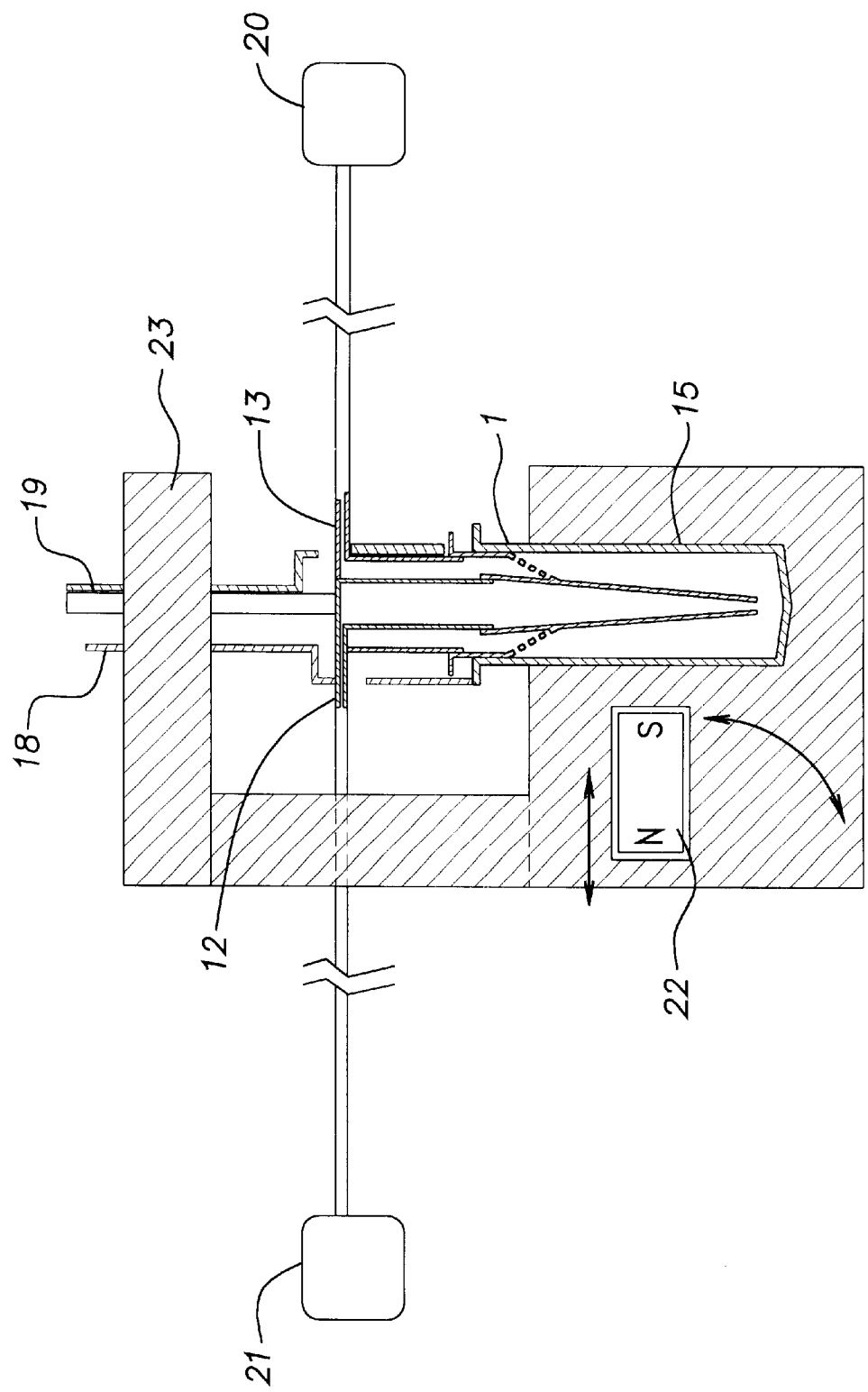
Figure 7:
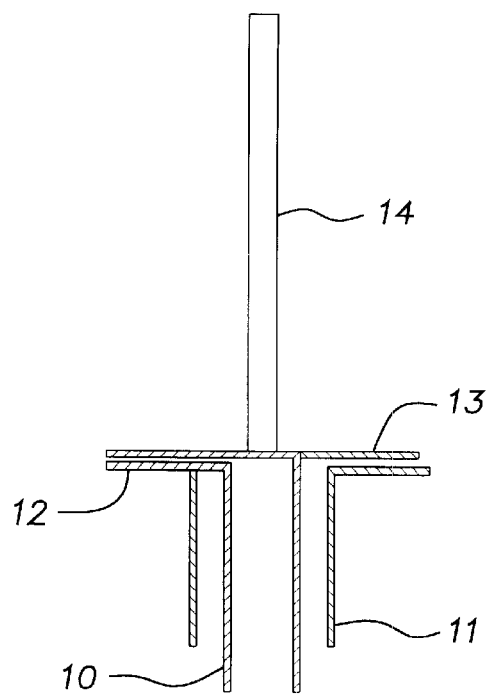
Figure 7:
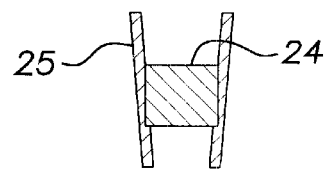
Figure 7:
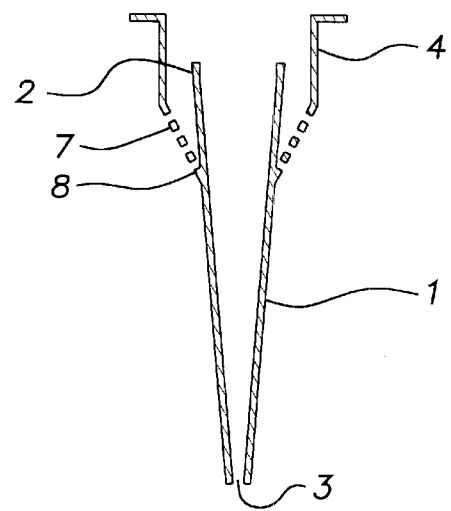

FIG. 3 shows a diagrammatic cross section through the device in accordance with FIG. 1 in conjunction with the connection piece in accordance with FIG. 2, FIG. 4 shows a diagrammatic cross section through the arrangement in accordance with FIG. 3 in conjunction with a reaction vessel, FIG. 5 shows a diagrammatic cross section through the arrangement in accordance with FIG. 4 in combination with a pipette tip discarding device, FIG. 6 shows a diagrammatic cross section through a washing device, and FIG. 7 shows a diagrammatic cross section through a device with a filtering element.

FIG. 1 shows a diagrammatic cross section through a device according to the invention. A conically tapering tube 1 is provided, in the vicinity of one of its ends, with a connection fitting 2, by means of which it can be fitted onto a connection or a multipassage pipette which operates in accordance with the reciprocating pump principle. A first opening 3 is provided at the other end. A second connection fitting 4 has a flange 5 which extends from the circumferential edge. The second connection fitting 4 also has a cylindrical section 6, which is adjoined by a conical section 7 which is connected to the outer wall of the tube 3. Second openings 8, which may be designed as nozzles, are provided in the region of the conical section 7. The cylindrical section 6 and the conical section 7 form an annular passage 9. The annular passage 9 is separate from the passage formed by the tube 1.

FIG. 2 shows a diagrammatic cross-sectional view through a connection. This is essentially formed from an inner connection tube 10 and an outer connection tube 11. The inner connection tube 10 is in communication with a first connection piece 12 and the outer connection tube 11 is in communication with a second connection piece 13. The connection pieces 12 and 13 may be connected, for example via hoses, to suitable pumps for delivering and discharging liquid.

FIG. 3 shows a diagrammatic cross section through the device in accordance with FIG. 1 in conjunction with the connection in accordance with FIG. 2. An element for attaching the device to a pipetting robot is denoted by 14.

FIG. 4 shows a diagrammatic cross section through the device in accordance with FIG. 3, this device having been inserted into a reaction vessel 15. The cylindrical section 6 bears tightly against the inner wall of the reaction vessel 15. The connection is achieved by means of frictional engagement or latching. However, the seal may also be achieved by means of a sealing lip or an O-ring. The reaction vessel has a volume in the range from 0.1–100 ml, preferably from 0.1–0.5 ml. The first opening 3 of the tube 1 is situated just above the bottom 16 of the reaction vessel 15.

FIG. 5 shows a diagrammatic cross section through the device in accordance with FIG. 4 together with a pipette tip discarding device 17. The connection which is held on the pipette tip discarding device 17 by means of the holding element 14 is connected to the device. A retaining element 18 extends from the pipette tip discarding device 17 to the top edge of the reaction vessel 15. A discarding device 19 extends from the pipette tip discarding device 17 as far as the vicinity of the flange 5.

FIG. 6 shows a diagrammatic cross-sectional view through the device in accordance with FIG. 5 in an automatic washing appliance. The appliance comprises a suction unit 21 which is connected to the first connection piece 12 and a metering unit 20 which is connected to the second connection piece 13. A movable permanent magnet 22 is provided in the vicinity of the reaction vessel 15. The pipette tip discarding device 17 is held in a holding arm 23. This may be a robot-controlled arm.

Finally, FIG. 7 shows a diagrammatic cross-sectional view through the device according to the invention with a filter attachment 24. A filtering element 25 is accommodated in the filter attachment 24. The filtering element 25 is designed in such a way that it can be fitted into the first connection fitting 2 and at the same time the inner connection tube 10 can be fitted into it.

The device functions as follows:

The device, which is generally produced from injection-molded plastic, is initially fitted onto the connection. This can be carried out automatically as a result of the arm of a pipetting robot simultaneously pressing the connection into the first connection fitting 2 and the second connection fitting 4 of the device, which is situated in a store.

Then, the device, if appropriate also by means of the pipetting robot, is fitted into the reaction vessel 15. A metering unit 20 is started up and washing solution is introduced, via the second connection piece 13, into the annular passage 9 and, from there, through the second openings 8, into the reaction vessel 15. After a predetermined time, the washing solution is sucked out and discarded via first opening 3, tube 1 and first connection piece 12 by starting up the suction unit 21. The operation can be repeated as often as desired. Prior to the suction operation, magnetic particles which are situated in the reaction vessel 15 can be drawn to one side of the vessel as a result of a movement of the permanent magnet 22, so that there is no possibility of the magnetic particles being sucked out inadvertently.

In order to explain the functioning of the device further, the isolation of DNA from a whole blood sample is described in the following example.

First of all, a lysis buffer and a washing buffer are produced using the method described by Boom et al. Magnetic glass particles produced by the FMC company are used as the solid phase. The volume of the reaction vessel is 2 ml.

20 μl of whole blood are treated with 1 ml of lysis buffer. 100 μl of the suspension formed are used as the solid phase. To wash the magnetic particles, the reaction vessel 15 is placed in a magnet separator (Boehringer-Mannheim, Order No.: 1 641 794). The supernatant is then sucked out using the device according to the invention, the reaction vessel 15 is removed from the magnet separator and the washing solution is added. The magnet separation is then performed again and the washing solution is sucked out. This operation is repeated twice, the device according to the invention being fixed on the reaction vessel 15 in the manner of a cover during the washing process. No contamination to the DNA was observed.

List of Reference Numerals

| | |
|---|---|
| 1 | Tube |
| 2 | First connection fitting |
| 3 | First opening |
| 4 | Second connection fitting |
| 5 | Flange |
| 6 | Cylindrical section |
| 7 | Conical section |
| 8 | Second opening |
| 9 | Annular passage |
| 10 | Inner connection piece |
| 11 | Outer connection piece |
| 12 | First connection piece |
| 13 | Second connection piece |
| 14 | Holding element |
| 15 | Reaction vessel |
| 16 | Bottom |
| 17 | Pipette tip discarding device |
| 18 | Retaining element |
| 19 | Discarding device |
| 20 | Metering unit |
| 21 | Suction unit |
| 22 | Permanent magnet |
| 23 | Holder for pipette tip discarding device |
| 24 | Filter attachment |
| 25 | Filtering element |

What is claimed is:

1. Device for the contamination-free delivery and discharge of liquid into and from a reaction vessel (15), said device comprising a tube (1), a first end of which is designed as a first connection fitting (2) for connection to a pipette or the like and a second end of which has a first opening (3), wherein the tube (1) is designed so as to taper conically toward the first opening (3), and a second connection fitting (4), which is in communication with at least a second opening (8), in the vicinity of the first end, said second connection fitting (4) comprising an outer wall forming an annular passage (9), which is separate from the passage formed by the tube (1) and which surrounds the tube (1).

2. Device according to claim 1, in which the first connection fitting (2) is situated inside the second connection fitting (4).

3. Device according to claim 2, in which the second connection fitting (4) has a flange (5).

4. Device according to claim 2, in which the second connection fitting (4) is in communication with an annular passage (9) which surrounds the tube (1).

5. Device according to claim 4, in which the annular passage (9) has a cylindrical section (6) in the vicinity of the second connection fitting (4).

6. Device according to claim 5, in which a conical section (7), which is connected to an outer wall of the tube (1), adjoins the cylindrical section (6).

7. Device according to claim 6, in which the second opening (8) is situated in the conical section (7).

8. Device according to claim 6, in which the cylindrical section (6) can be fitted into the reaction vessel (15).

9. Device according to claim 8, in which the second opening (8), when the device has been fitted completely onto the reaction vessel (15), is at a distance of from 1–10 mm from a top edge of the reaction vessel.

10. Device according to claim 9, in which the first opening (3), when the device has been fitted completely onto the reaction vessel (15), is at a distance of from 0.1–5 mm from a bottom (16) of the reaction vessel.

11. Device according to claim 1, in which a filtering element (25), which can be fitted onto the first connection fitting (2), is provided.

12. Device according to claim 1, in which the reaction vessel (15) forms part of a titration plate which has 96 reaction vessels (15).

13. Pipette, in particular multipassage pipette, having a device according to any one of the preceding claims.

14. Pipetting robot having a device according to any one of claims 1–13.

15. Use of the device, the pipette on the pipetting robot according to any one of the preceding claims for the analysis and/or isolation of nucleic acids.

16. Device according to claim 9, wherein the second opening (8), when the device has been fitted completely onto the reaction vessel (15), is at a distance of from 2–5 mm from the top edge of the reaction vessel.

17. Device according to claim 10, wherein the first opening (3), when the device has been fitted completely onto the reaction vessel (15), is at a distance of from 0.5–2 mm from the bottom (16).

18. Device for the contamination-free delivery and discharge of liquid into and from a reaction vessel (15), said device comprising a tube (1), a first end of which is designed as a first connection fitting (2) for connection to a pipette or the like and a second end of which has a first opening (3), wherein the tube (1) is designed so as to taper conically toward the first opening (3), a filtering element (25) which can be fitted onto the first connection fitting (2), and a second connection fitting (4), which is in communication with at least a second opening (8), in the vicinity of the first end, said second connection fitting (4) comprising an outer wall forming an annular passage (9), which is separate from the passage formed by the tube (1) and which surrounds the tube (1).

19. Device according to claim 18, in which the first connection fitting (2) is situated inside the second connection fitting (4).

20. Device according to claim 19, in which the second connection fitting (4) has a flange (5).

21. Device according to claim 19, in which the second connection fitting (4) is in communication with an annular passage (9) which surrounds the tube (1).

22. Device according to claim 21, in which the annular passage (9) has a cylindrical section (6) in the vicinity of the second connection fitting (4).

23. Device according to claim 22, in which a conical section (7), which is connected to an outer wall of the tube (1), adjoins the cylindrical section (6).

24. Device according to claim 23, in which the second opening (8) is situated in the conical section (7).

25. Device according to claim 23, in which the cylindrical section (6) can be fitted into the reaction vessel (15).

26. Device according to claim 25, in which the second opening (8), when the device has been fitted completely onto the reaction vessel (15), is at a distance of from 1–10 mm from a top edge of the reaction vessel.

27. Device according to claim 26, wherein the second opening (8), when the device has been fitted completely onto the reaction vessel (15), is at a distance of from 2–5 mm from the top edge of the reaction vessel.

28. Device according to claim 26, in which the first opening (3), when the device has been fitted completely onto the reaction vessel (15), is at a distance of from 0.1–5 mm from a bottom (16) of the reaction vessel.

29. Device according to claim 28, wherein the first opening (3), when the device has been fitted completely onto the reaction vessel (15), is at a distance of from 0.5–2 mm from the bottom (16).

30. Device according to claim 16, in which the reaction vessel (15) forms part of a titration plate which has 96 reaction vessels (15).

\* \* \* \* \*

UNITED STATES PATENT AND TRADEMARK OFFICE
CERTIFICATE OF CORRECTION

PATENT NO. : 6,379,624 B1
DATED : April 30, 2002
INVENTOR(S) : Hans Lange

It is certified that error appears in the above-identified patent and that said Letters Patent is hereby corrected as shown below:

<u>Column 5,</u>
Line 5, please delete "any".
Line 6, please delete "any".
Line 9, please delete "any".

Signed and Sealed this

Eighth Day of October, 2002

*Attest:*

JAMES E. ROGAN
*Director of the United States Patent and Trademark Office*

*Attesting Officer*